(12) United States Patent
Li et al.

(10) Patent No.: US 11,295,450 B2
(45) Date of Patent: Apr. 5, 2022

(54) SYSTEM AND METHOD FOR MEDICAL IMAGE VISUALIZATION

(71) Applicant: SHANGHAI UNITED IMAGING HEALTHCARE CO., LTD., Shanghai (CN)

(72) Inventors: Liu Li, Shanghai (CN); Jun Wan, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 9 days.

(21) Appl. No.: 16/716,677

(22) Filed: Dec. 17, 2019

(65) Prior Publication Data

US 2020/0226761 A1   Jul. 16, 2020

(30) Foreign Application Priority Data

Dec. 21, 2018   (CN) .......................... 201811578474.9

(51) Int. Cl.
*G06T 7/11* (2017.01)
*G06T 7/174* (2017.01)
*G06T 11/00* (2006.01)

(52) U.S. Cl.
CPC ................ *G06T 7/11* (2017.01); *G06T 7/174* (2017.01); *G06T 11/001* (2013.01); *G06T 2207/10072* (2013.01); *G06T 2207/20012* (2013.01); *G06T 2207/20132* (2013.01); *G06T 2210/41* (2013.01)

(58) Field of Classification Search
CPC ......... G06T 7/11; G06T 7/174; G06T 11/001; G06T 2210/41; G06T 2207/20132; G06T 2207/10072; G06T 11/00; A61B 6/469
See application file for complete search history.

(56) References Cited

U.S. PATENT DOCUMENTS

| 8,120,696 B2 * | 2/2012 | Jerdev | G03B 7/09979 |
| | | | 348/349 |
| 2013/0137984 A1 * | 5/2013 | Takagi | A61B 8/14 |
| | | | 600/443 |
| 2015/0110375 A1 * | 4/2015 | Habets | G06T 7/11 |
| | | | 382/131 |
| 2016/0329033 A1 | 11/2016 | Woo et al. | |

(Continued)

FOREIGN PATENT DOCUMENTS

| CN | 101277411 B | 10/2011 |
| CN | 102254520 A | 11/2011 |
| CN | 103714185 B | 2/2017 |

*Primary Examiner* — Grace Q Li
(74) *Attorney, Agent, or Firm* — Metis IP LLC

(57) ABSTRACT

The present disclosure provides a system and method for medical image visualization. The method may include obtaining original image data of a subject, the original image data including a first region of interest (ROI) and a second ROI. The method may also include generating first image data associated with the first ROI according to a first instruction, and causing the first ROI to be displayed on a display device as a first image based on the first image data. The method may further include generating, according to a second instruction, second image data corresponding to a target region that includes the second ROI, updating the first image data based on the second image data, and causing the second ROI to be displayed on the display device as a second image based on the updated first image data.

20 Claims, 9 Drawing Sheets

(56) References Cited

U.S. PATENT DOCUMENTS

| | | | | |
|---|---|---|---|---|
| 2016/0346043 A1* | 12/2016 | Jaquet | ............... | A61B 34/25 |
| 2020/0013152 A1* | 1/2020 | Bohm | ............... | A61B 6/481 |
| 2020/0281562 A1* | 9/2020 | Haase | ............... | A61B 6/504 |

* cited by examiner

SYSTEM AND METHOD FOR MEDICAL IMAGE VISUALIZATION

CROSS-REFERENCE TO RELATED APPLICATIONS

This application claims priority to Chinese Application No. 201811578474.9, filed on Dec. 21, 2018, the contents of which are hereby incorporated by reference.

TECHNICAL FIELD

The present disclosure generally relates to systems and methods for image visualization, and more particularly, to systems and methods for a local region update of a medical image.

BACKGROUND

In a visualization process of medical image data, the medical image data is rendered by a graphic processor unit (GPU) and displayed on a display device (e.g., a screen). In actual applications, a user may be interested in different regions at different stages in a workflow. Thus, a plurality of regions of interest (ROIs) need to be displayed on the display device. Conventional methods for updating image data when the plurality ROIs are displayed are time-consuming and inefficient. Thus, it is desirable for systems and methods for displaying different ROIs more efficiently.

SUMMARY

In a first aspect of the present disclosure, a system is provided. The system may include at least one storage medium including a set of instructions, and at least one processor in communication with the at least one storage medium. When executing the set of instructions, the at least one processor may be configured to direct the system to perform operations including obtaining original image data of a subject, the original image data including a first region of interest (ROI) and a second ROI; generating first image data associated with the first ROI according to a first instruction; causing the first ROI to be displayed on a display device as a first image based on the first image data; generating, according to a second instruction, second image data corresponding to a target region that includes the second ROI; updating the first image data based on the second image data; and causing the second ROI to be displayed on the display device as a second image based on the updated first image data.

In a second aspect of the present disclosure, a method is provided. The method may be implemented on a computing apparatus having at least one processor and at least one computer-readable storage device. The method may include obtaining original image data of a subject, the original image data including a first ROI and a second ROI; generating first image data associated with the first ROI according to a first instruction; causing the first ROI to be displayed on a display device as a first image based on the first image data; generating, according to a second instruction, second image data corresponding to a target region that includes the second ROI; updating the first image data based on the second image data; and causing the second ROI to be displayed on the display device as a second image based on the updated first image data.

In a third aspect of the present disclosure, a non-transitory computer readable medium, comprising at least one set of instructions, wherein when executed by at least one processor of a computing device, the at least one set of instructions causes the computing device to perform a method may be provided. The method may include obtaining original image data of a subject, the original image data including a first ROI and a second ROI; generating first image data associated with the first ROI according to a first instruction; causing the first ROI to be displayed on a display device as a first image based on the first image data; generating, according to a second instruction, second image data corresponding to a target region that includes the second ROI; updating the first image data based on the second image data; and causing the second ROI to be displayed on the display device as a second image based on the updated first image data.

In some embodiments, the causing the first ROI to be displayed on the display device as a first image based on the first image data may include causing a rendering device associated with the display device to render the first image data; and causing the display device to display the first ROI in the first image based on the rendered first image data.

In some embodiments, the second instruction is generated based on the first image.

In some embodiments, the causing the second ROI to be displayed on the display device as a second image based on the updated first image data may include causing a rendering device associated with the display device to render the updated first image data; and causing the display device to display the second ROI in the second image based on the rendered updated first image data.

In some embodiments, the operations may further include segmenting the first ROI from the original image data according to the first instruction; and segmenting the second ROI from the original image data according to the second instruction.

In some embodiments, the target region has a discrete shape that is the same as the second ROI or a block shape encompassing the second ROI.

In some embodiments, the shape of the target region is determined based at least in part on a shape of the second ROI.

In some embodiments, the original image data includes volume data, and the first image data and the second image data includes mask data.

In some embodiments, the causing the first ROI to be displayed on the displaying device as a first image based on the first image data may include causing the first ROI to be displayed on the displaying device in a first color different from other regions in the first image.

In some embodiments, the causing the second ROI to be displayed on the displaying device as a second image based on the updated first image data may include causing the second ROI to be displayed on the displaying device in a second color different from the first color in the second image.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by another expression if they may achieve the same purpose.

Figure 2:
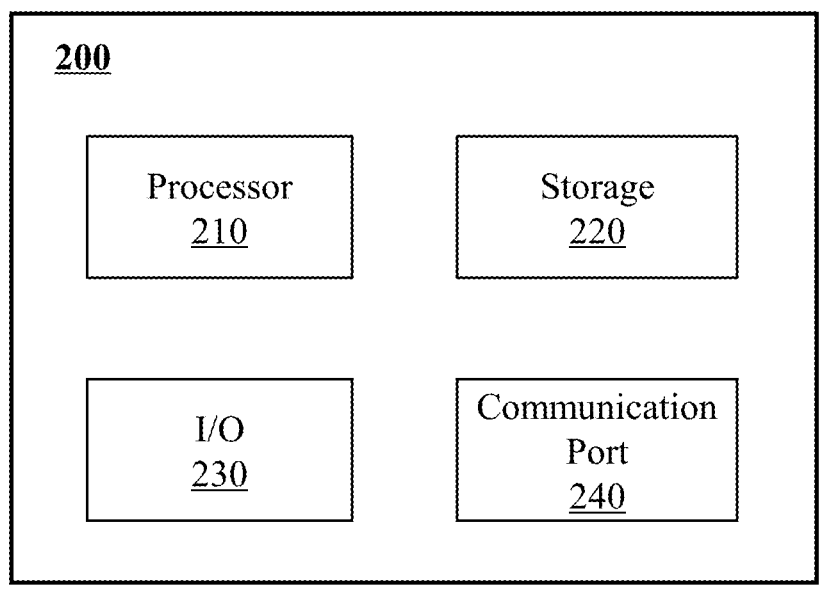
FIG. 2 is a schematic diagram illustrating hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an erasable programmable read-only memory (EPROM). It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include" and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

Provided herein are systems and components for non-invasive imaging and/or treatment, such as for disease diagnosis, treatment or research purposes. In some embodiments, the system may be a radiation therapy system, a computed tomography (CT) system, an emission computed tomography (ECT) system, an X-ray photography system, a positron emission tomography (PET) system, or the like, or any combination thereof. For illustration purposes, the disclosure describes systems and methods for radiation therapy. The term "image" used in this disclosure may refer to a 2D image, a 3D image, or a 4D image. In some embodiments, the term "image" may refer to an image of a region, e.g., a region of interest (ROI), of a patient. The term "region of interest" or "ROI" used in this disclosure may refer to a part of an image along a line, in two spatial dimensions, in three spatial dimensions, or any of the proceeding as they evolve as a function of time. The image may be a CT image, PET image, an MR image, a fluoroscopy image, an ultrasound image, etc. This is not intended to limit the scope of the present disclosure. For persons having ordinary skills in the art, a certain number of variations, changes, and/or modifications may be deduced under the guidance of the present disclosure. Those variations, changes, and/or modifications do not depart from the scope of the present disclosure.

According to an aspect of the present disclosure, a system and method for displaying image data of multiple ROIs. The method may include obtaining image data including a first ROI and a second ROI of a subject. First image data associated with the first ROI may be generated according to a first instruction, and the first ROI may be caused to be displayed on a display device as a first image based on the first image data. Second image data associated with a target region including the second ROI may be generated according to a second instruction, the first image data may be updated based on the second image data, and the second ROI may be caused to be displayed on the display device as a second image based on the updated first image data.

In the image data visualization process proposed by the present disclosure, the entire image data to be rendered (e.g., the first image data) may not be updated when different ROIs are displayed in different images. Instead, a local region update operation may be performed on the image data to be rendered according to actual requirements, thereby speeding up the image date update process and improve the image data update efficiency.

Figure 1:
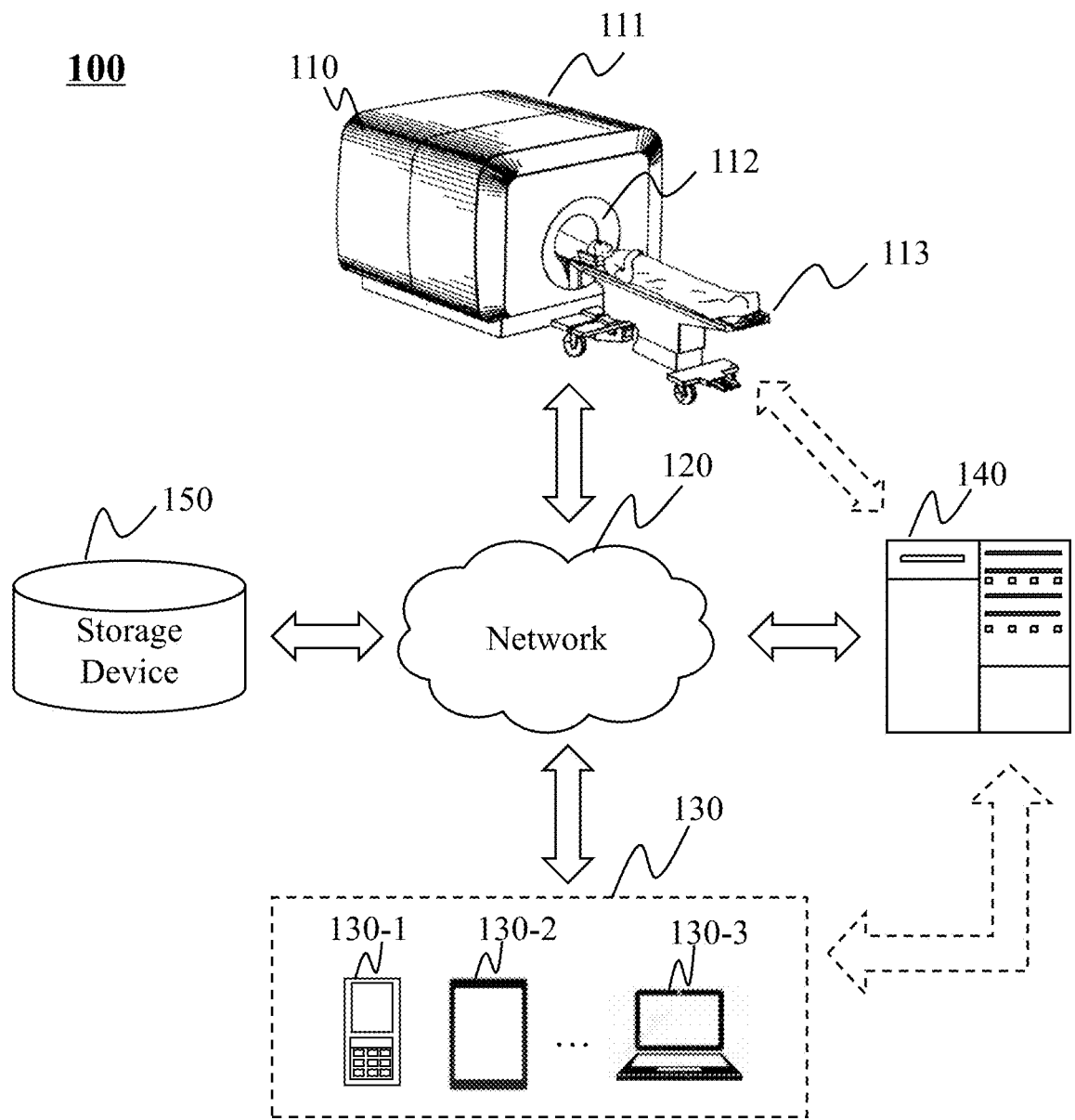
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. This is understood that the systems and methods for displaying image data of multiple ROIs are also applicable in other systems, e.g., a treatment system. The following descriptions are provided, unless otherwise stated expressly, with reference to an imaging system for illustration purposes and not intended to be limiting. As illustrated, the imaging system 100 may include an imaging scanner 110, a network 120, one or more terminals 130, a processing device 140, and a storage device 150. The components in the imaging system 100 may be connected in various ways. Merely by way of example, as illustrated in FIG. 1, the imaging scanner 110 may be connected to the processing device 140 through the network 120. As another example, the imaging scanner 110 may be connected with the processing device 140 directly as indicated by the bi-directional arrow in dotted lines linking the imaging scanner 110 and the processing device 140. As a further example, the storage device 150 may be connected with the processing device 140 directly (not shown in FIG. 1) or through the network 120. As still a further example, one or more terminal(s) 130 may be connected with the processing device 140 directly (as indicated by the bi-directional arrow in dotted lines linking the terminal(s) 130 and the processing device 140) or through the network 120.

The imaging scanner 110 may scan a subject or a portion thereof that is located within its detection region, and generate imaging data relating to the (part of) subject. In some embodiments, the subject may include a body, a substance, or the like, or a combination thereof. In some embodiments, the subject may include a specific portion of a body, such as the head, the thorax, the abdomen, or the like, or a combination thereof. In some embodiments, the subject may include a specific organ, such as the heart, the esophagus, the trachea, the bronchus, the stomach, the gallbladder, the small intestine, the colon, the bladder, the ureter, the uterus, the fallopian tube, etc. In some embodiments, the imaging scanner 110 may include a computed tomography (CT) scanner, a positron emission computed tomography (PET) scanner, a single-photon emission computed tomography (SPECT) scanner, a magnetic resonance (MR) scanner, an ultrasonic scanner, an emission computed tomography (ECT) scanner, or the like. In some embodiment, the imaging scanner 110 may be a multi-modality device including two or more scanners listed above. For example, the imaging scanner 110 may be a PET-CT scanner, a PET-MR scanner, etc.

Merely for illustration purposes, a CT scanner may be provided as an example for better understanding the imaging scanner 110, which is not intended to limit the scope of the present disclosure. The CT may include a gantry 111, a detecting region 112, and a bed 113. The gantry 111 may support one or more radiation sources and/or detectors (not shown). A subject may be placed on the bed 113 for CT scan. When the imaging scanner 110 performs a CT scan, a radiation source may emit radioactive rays to the subject, and one or more detectors may detect radiation rays emitted from the detecting region 112. The radiation rays emitted from the detecting region 112 may be used to generate CT data (also referred to as CT image data). The one or more detectors used in CT scan may include a scintillation detector (e.g., a cesium iodide detector), a gas detector, etc.

The processing device 140 may process data and/or information obtained and/or retrieve from the imaging scanner 110, the terminal(s) 130, the storage device 150 and/or other storage devices. For example, the processing device 140 may obtain image data from the imaging scanner 110, and reconstruct an image of the subject based on the image data. As another example, the processing device 140 may generate first image data associated with the first ROI according to a first instruction, and cause the first ROI to be displayed on a display device as a first image based on the first image data. As a further example, the processing device 140 may generate second image data associated with a second ROI according to a second instruction, update the first image data based on the second image data, and cause the second ROI to be displayed on the display device as a second image based on the updated first image data. In some embodiments, the processing device 140 may be a single server or a server group. The server group may be centralized or distributed. In some embodiments, the processing device 140 may be local or remote. For example, the processing device 140 may access information and/or data stored in the imaging scanner 110, the terminal(s) 130, and/or the storage device 150 via the network 120. As another example, the processing device 140 may be directly connected with the imaging scanner 110, the terminal(s) 130, and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing apparatus 200 having one or more components illustrated in FIG. 2 in the present disclosure.

The storage device 150 may store data and/or instructions. In some embodiments, the storage device 150 may store data obtained from the imaging scanner 110, the terminal(s) 130, and/or the processing device 140. For example, the storage device 150 may store scanning data, signals, images, videos, algorithms, texts, instructions, program codes, etc. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected with the network 120 to communicate with one or more components of the imaging system 100 (e.g., the processing device 140, the terminal(s) 130, etc.). One or more components of the imaging system 100 may access the data or instructions stored in the storage device 150 via the network 120. In some embodiments, the storage device 150 may be directly connected with or communicate with one or more components of the imaging system 100 (e.g., the processing device 140, the terminal(s) 130, etc.). In some embodiments, the storage device 150 may be part of the processing device 140.

The terminal(s) 130 may include a mobile device 130-1, a tablet computer 130-2, a laptop computer 130-3, or the like, or any combination thereof. In some embodiments, the mobile device 140-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smartwatch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a Hololens, a Gear VR, etc. In some embodiments, the terminal(s) 130 may remotely operate the imaging scanner 110. In some embodiments, the terminal(s) 130 may operate the imaging scanner 110 via a wireless connection. In some embodiments, the terminal(s) 130 may receive information and/or instructions inputted by a user, and send the received information and/or instructions to the imaging scanner 110 or the processing device 140 via the network 120. In some embodiments, the terminal(s) 130 may receive data and/or information from the processing device 140. In some embodiments, the terminal(s) 130 may be part of the processing device 140. In some embodiments, the terminal(s) 130 may be omitted.

The network 120 may include any suitable network that can facilitate the exchange of information and/or data for the imaging system 100. In some embodiments, one or more components of the imaging system 100 (e.g., the imaging scanner 110, the terminal(s) 130, the processing device 140, or the storage device 150) may communicate information and/or data with one or more other components of the imaging system 100 via the network 120. In some embodiments, the network 120 may be any type of wired or wireless network, or a combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected with the network 120 to exchange data and/or information.

It should be noted that the above description of the imaging system 100 is merely provided for the purposes of illustration, not intended to limit the scope of the present disclosure. For persons having ordinary skills in the art, components contained in the imaging system 100 may be combined or adjusted in various ways, or connected with other components as sub-systems, and various variations and modifications may be conducted under the teaching of the present disclosure. However, those variations and modifications may not depart the spirit and scope of this disclosure. For example, the imaging scanner 110 may be a standalone device external to the imaging system 100, and the imaging system 100 may be connected to or in communication with the imaging scanner 110 via the network 120. All such modifications are within the protection scope of the present disclosure.

FIG. 2 is a schematic diagram illustrating hardware and/or software components of an exemplary computing apparatus 200 on which the processing device 140 may be implemented according to some embodiments of the present disclosure. As illustrated in FIG. 2, the computing apparatus 200 may include a processor 210, a storage 220, an input/output (I/O) 230, and a communication port 240.

The processor 210 may execute computer instructions (program code) and perform functions of the processing device 140 in accordance with techniques described herein. The computer instructions may include, for example, routines, programs, objects, components, signals, data structures, procedures, modules, and functions, which perform particular functions described herein. For example, the processor 210 may process data obtained from the imaging scanner 110, the terminal(s) 130, the storage device 150, and/or any other component of the imaging system 100. Specifically, the processor 210 may process image data obtained from the imaging scanner 110. For example, the processor 210 may generate an image based on the image data and identify a structure of a target classification from the image. In some embodiments, the image may be stored in the storage device 150, the storage 220, etc. In some embodiments, the image may be displayed on a display device by the I/O 230. In some embodiments, the processor 210 may perform instructions obtained from the terminal(s) 130. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing apparatus 200. However, it should be noted that the computing apparatus 200 in the present disclosure may also include multiple processors. Thus operations and/or method steps that are performed by one processor as described in the present disclosure may also be jointly or separately performed by the multiple processors. For example, if in the present disclosure the processor of the computing apparatus 200 executes both operation A and operation B, it should be understood that operation A and operation B may also be performed by two or more different processors jointly or separately in the computing apparatus 200 (e.g., a first processor executes operation A and a second processor executes operation B, or the first and second processors jointly execute operations A and B).

The storage 220 may store data/information obtained from the imaging scanner 110, the terminal(s) 130, the storage device 150, or any other component of the imaging system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 140 for determining a target classification of a structure of a subject.

The I/O 230 may input or output signals, data, and/or information. In some embodiments, the I/O 230 may enable user interaction with the processing device 140. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 120) to facilitate data communications. The communication port 240 may establish connections between the processing device 140 and the imaging scanner 110, the terminal(s) 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
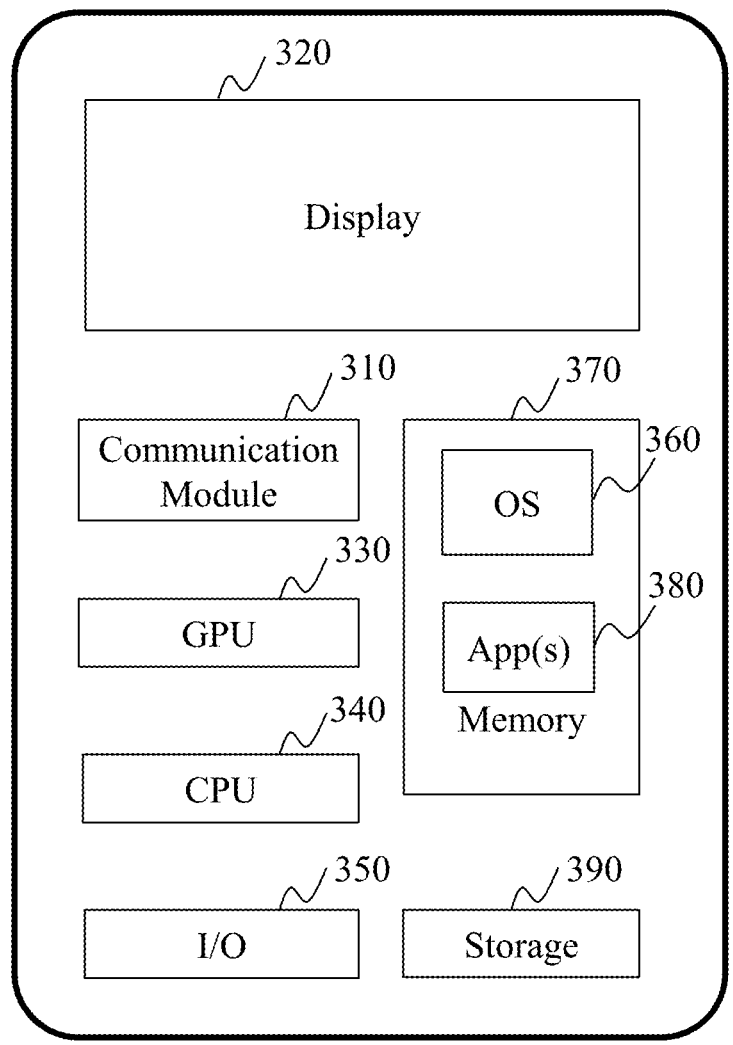
FIG. 3 is a schematic diagram illustrating hardware and/or software components of an exemplary mobile device according to some embodiments of the present disclosure.

FIG. 3 is a schematic diagram illustrating hardware and/or software components of an exemplary mobile device 300 according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 370, and a storage 390. In some embodiments, any other suitable component, including but not limited to a system bus or a controller (not shown), may also be included in the mobile device 300. In some embodiments, a mobile operating system 360 (e.g., iOS, Android, Windows Phone, etc.) and one or more applications 380 may be loaded into the memory 370 from the storage 390 in order to be executed by the CPU 340. The applications 380 may include a browser or any other suitable mobile apps for receiving and rendering information relating to data processing or other information from the processing device 140. User interactions with the information stream may be achieved via the I/O 350 and provided to the processing device 140 and/or other components of the imaging system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an imaging report as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
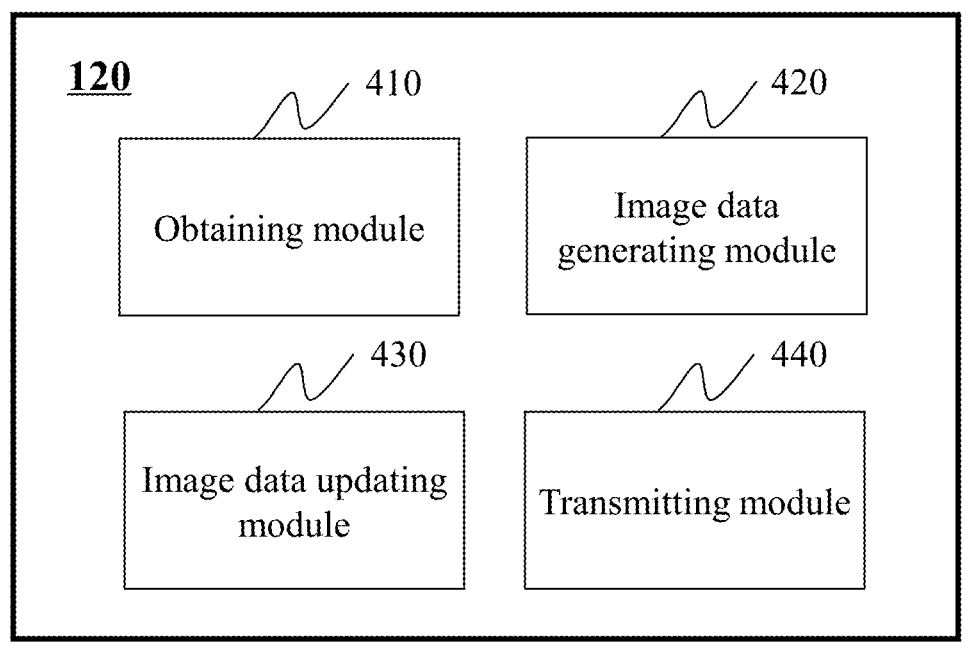
FIG. 4 is a block diagram illustrating an exemplary processing device according to some embodiments of the present disclosure.

FIG. 4 is a block diagram illustrating an exemplary processing device according to some embodiments of the present disclosure. The processing device 140 may include an obtaining module 410, an image data generating module 420, an image data updating module 430, and a transmitting module 440. One or more of the modules of the processing device 140 may be interconnected. The connection(s) may be wireless or wired. At least a portion of the processing device 140 may be implemented on a computing apparatus as illustrated in FIG. 2 or a mobile device as illustrated in FIG. 3.

The obtaining module 410 may obtain data. The obtaining module 410 may obtain data from the imaging scanner 110, the terminal(s) 130, the processing device 140, the storage device 150, or any devices or components capable of storing data via the network 120. For example, the obtaining module 410 may obtain data from a medical cloud data center (not shown) via the network 120. The obtained data may include scanning data (e.g., original image data), processed results (e.g., first image data, second image data, updated first image data, etc.), user instructions (e.g., a first instruction for displaying a first ROI on a display device), algorithms (e.g., an image segmentation algorithm), models (e.g., a neural network model), program codes, or the like, or a combination thereof. In some embodiments, the obtaining module 410 may obtain original image data of a subject. The obtaining module 410 may obtain the original image data from a medical imaging system, such as a magnetic resonance imaging (MRI) system, a computed tomography (CT) system, a digital X-ray imaging system, an ultrasound imaging system, a positron emission computed tomography (PET) system, a PET-MR system, a PET-CT system, etc. In some embodiments, the structure of the subject may be a specific portion of a body of the subject, such as the head, the thorax, the abdomen, or the like, or a combination thereof. In some embodiments, the structure of the subject may be a specific organ of the subject, such as lungs, the heart, the esophagus, the trachea, the bronchus, the stomach, the gallbladder, the small intestine, the colon, the bladder, the ureter, the uterus, the fallopian tube, etc.

The obtaining module 410 may transmit the obtained data to a storage device (e.g., the storage device 150, etc.) for storage. In some embodiments, the obtaining module 410 may transmit the obtained data to a computing device (including, for example, the image data generating module 420, the image data updating 430, etc.) for processing.

The image data generating module 420 may generate image data associated with a ROI. In some embodiments, the image data generating module 420 may generate first image associated with a first ROI. The first ROI may be segmented from a region corresponding to the original image data. In some embodiments, the first ROI may be segmented by the image data generating module 420 automatically. Specifically, the image data generating module 420 may employ various image segmentation algorithms including but not limited to a threshold-based segmentation algorithm, an edge-based segmentation algorithm, a region-based segmentation algorithm, a graph theory-based segmentation algorithm, an energy functional-based segmentation algorithm, a wavelet-based segmentation algorithm, a neural network-based segmentation algorithm, etc. In some embodiments, the first ROI may be segmented by a user manually. For example, a doctor may segment a vertebra from an image of a human body manually. In some embodiments, the first ROI may be segmented using a semi-automatic method. For example, a user may specify a seed point within an outline of the first ROI, and the image data generating module 420 may segment the first ROI using a region growing algorithm according to the seed point specified by the user.

In some embodiments, the image data generating module 420 may designate the image data corresponding to the first ROI in the medical image data as the first image data. Alternatively, the image data generating module 420 may determine a region encompassing the first ROI, and designate image data corresponding to the region encompassing the first ROI as the first image data. The first image data including the first ROI may be displayed as a first image on a display device.

In some embodiments, the image data generating module 420 may generate second image associated with a second ROI. In some embodiments, the second ROI may be segmented from the first image. In some embodiments, the second ROI may be segmented by the image data generating module 420 automatically. In some embodiments, the second ROI may be segmented in the first image by a user manually. In some embodiments, the second ROI may be segmented using a semi-automatic method.

In some embodiments, the image data generating module 420 may determine a target region based on the second ROI. The target region may include the second ROI. In some embodiments, the shape of the target region may be determined based at on a shape of the second ROI. In some embodiments, elements (pixels or voxels) constituting the second ROI may have a larger degree of aggregation. For example, a dispersion degree between the elements calculated based on coordinates of the elements may be larger than a preset threshold. The second ROI may be determined to have a block shape. In this case, the target region may have a block shape encompassing the second ROI. In some embodiments, elements (pixels or voxels) constituting the second ROI may have a smaller degree of aggregation, such as scattered pixels. For example, the dispersion degree between the elements calculated based on coordinates of the elements may be smaller than or equal to the preset threshold. The second ROI may be determined to have a discrete shape. In this case, the target region may have a discrete shape that is the same as the second ROI. The image data generating module 420 may determine image data corresponding to the target region as the second image data.

The image data updating module 430 may update image data. In some embodiments, the image data updating module 430 may update the first image data based on the second image data. In some embodiments, the target region may be within the first ROI. The first image data may be updated by substituting image data corresponding to the target region in the first image data by the second image data. In some embodiments, the first ROI and the target region may be isolated regions independent from each other. The first image data may be updated by adding the second image data into the first image data. In some embodiments, the first ROI and the target region may be partially overlap. One or more overlapping regions of the first ROI and the target region may be determined. The first image data may be updated by adding the second image data into the first image data and removing a portion of the first image data that corresponds to the overlapping region from the first image data.

The transmitting module 440 may transmit image data to a display device. In some embodiments, the transmitting module 440 may transmit the first image data and/or updated first image data to the display device. After the transmitting module 440 transmits the first image data to the display device, the first ROI may be caused to be displayed on the display device as the first image. In some embodiments, the transmitting module 440 may transmit the first image data to the GPU of the display device (e.g., the GPU 330 in mobile device 300 as shown in FIG. 3). The first image data may be rendered by the GPU, and the first ROI may be displayed on a screen of the display device (such as the display 320 in FIG. 3).

After the transmitting module 440 transmits the updated first image data to the display device, the second ROI may be caused to be displayed on the display device as the second image. In some embodiments, the transmitting module 440 may transmit the updated first image data to the GPU of the display device (e.g., the GPU 330 in mobile device 300 as shown in FIG. 3). The updated first image data may be rendered by the GPU, and the second ROI may be displayed on a screen of the display device (such as the display 320 in FIG. 3).

It should be noted that the above descriptions of the processing device 140 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the processing device 140 may include one or more other modules. In some embodiments, two or more units in the processing device 140 may form one module. However, those variations and modifications also fall within the scope of the present disclosure.

Figure 5:
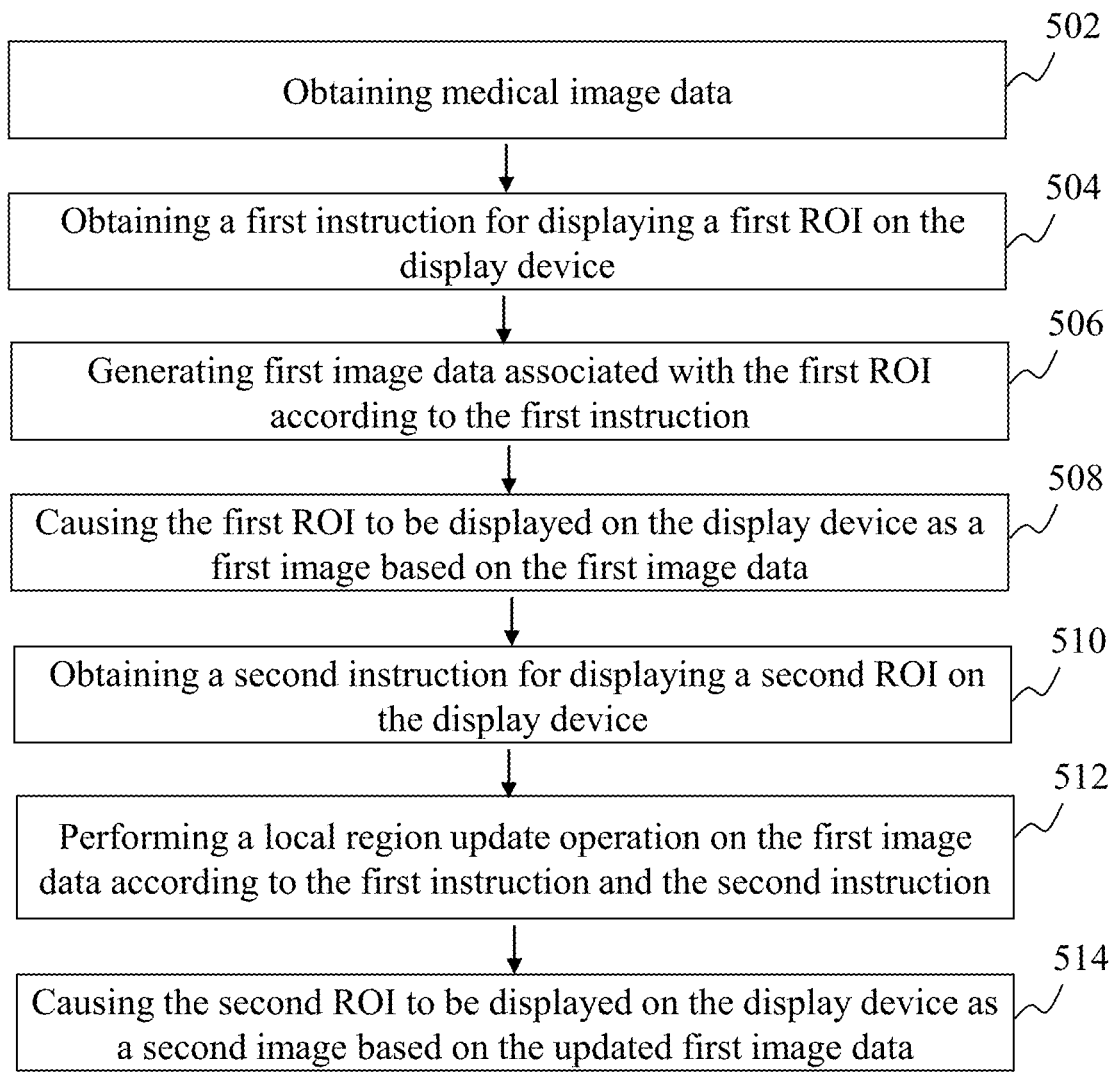
FIG. 5 is flowchart illustrating an exemplary process for displaying image data of multiple ROIs according to some embodiments of the present disclosure.

FIG. 5 is flowchart illustrating an exemplary process for displaying image data of multiple ROIs according to some embodiments of the present disclosure. In some embodiments, at least a portion of the process 500 may be executed by the processing device 140 (e.g., implemented in the computing apparatus 200 shown in FIG. 2, the processing device illustrated in FIG. 4). In some embodiments, the process 500 may be executed by a cloud server so as to reduce the working load of the processing device 140. In some embodiments, at least a portion of the process 500 may be executed by a terminal device (e.g., the mobile device 300 shown in FIG. 3) embodying software and/or hardware.

In 502, medical image data may be obtained. In some embodiments, the medical image data may be obtained by the obtaining module 410.

The medical image data may be two-dimensional (2D) image data or three-dimensional (3D) image data. In some embodiments, the medical image data may be original image data related to an entire body of a subject (e.g., a human or an animal) or a portion thereof (e.g., an organ or tissue). The organs may include, for example, the brain, the lungs, the heart, the kidneys, the liver, or the like. The tissue may include, for example, epithelial tissue, connective tissue, neural tissue, muscle tissue, or the like. The medical image data in the present disclosure may have various types including but not limited to, computed tomography (CT) image data, emission computed tomography (ECT) image data, magnetic resonance (MR) image data, ultrasound image data, positron emission tomography (PET) image data, or the like. The medical image data may include at least two ROIs including, for example, a first ROI, a second ROI, a third ROI, etc. Taking medical image data of the brain as an example, the medical image data of the brain may include ROIs of the entire brain, the thalamus, the putamen, the insula, the thalamus, the globus pallidus, the frontal lobe, the parietal lobe, the pituitary, the cerebrovascular, etc. Positions between each two of the ROIs may be in various relationships, such as partially overlapping, independent of each other, containment, or the like. In some embodiments, the processing device 140 may obtain the medical image data from the imaging scanner 110. In some embodiments, the processing device 140 may obtain the medical image data from the storage device 150.

In some embodiments, after the processing device 140 obtains the medical image data, the processing device 140 may control a display device (such as the terminal(s) 130 in FIG. 1, the mobile device 300 in FIG. 3, etc.) to display one or more images corresponding to the medical image data. In some embodiments, the display device may include a graphics processing unit (GPU) (e.g., the GPU 330 of the mobile device 300 as shown in FIG. 3). The processing device 140 may transmit the obtained and/or processed medical image data to the GPU, and the medical image data may be rendered by the GPU and displayed on the display device (such as the display 320 in FIG. 3), such that a user may view an image corresponding to the medical image data. In some embodiments, the processing device 140 may be embodied in the display device, and the processing device 140 may send the obtained and/or processed medical image data to the GPU within the display device, and an image corresponding to the medical image data may be displayed on, for example, a screen, after being rendered by the GPU.

In some embodiments, the medical image data may include volume data and mask data. The volume data may refer to raw image data obtained through a scanning device (such as the imaging scanner 110) by scanning a human or an animal or a portion thereof. The mask data may refer to data used to process the volume data in order to achieve a specific display effect. For example, CT volume data may be obtained by scanning a patient lying on a bed of a CT scanner. Since the density of the bed is different from that of human tissue, the doctor's observation at certain angles may be affected by the presence of the bed. In this case, the CT volume data may need to be processed using mask data such that the bed may not be present in a displayed image. As another example, doctors may often use computed tomography angiography (CTA) volume data of the brain to observe and diagnose diseases related to blood vessels (e.g., a cerebral artery) in the brain. However, the blood vessels in the brain may be surrounded by various soft tissue, skulls, facial muscles, etc. Thus, it may be needed to process the CTA volume data using the mask data such that the images of the soft tissue, the skulls, the facial muscles, etc., may be removed from the displayed image. In some embodiments, the mask data may have a same size as the volume data. For example, if the size of the volume is 512×512×512, the mask data may be three-dimensional data having a size of 512×512×512. The processing device 140 may process the volume data with the mask data, and send the processed volume data to the GPU for rendering so as to obtain a specific display effect.

In 504, a first instruction for displaying a first ROI on the display device (also referred to as first ROI display instruction) may be obtained. In some embodiments, the first instruction may be obtained by the obtaining module 410.

The first instruction may direct the imaging system 100 to display the first ROI in the medical image data on the display device. In some embodiments, the first ROI may be a part of a region corresponding to the medical image data. As for the region corresponding to the medical image data obtained in 502, a user may be interested in, for example, a part of the region in some cases. If the medical image data is visually presented to the user indiscriminately, the user may have difficulties to observe the part of the region that he/she is interested in. For example, the medical image data obtained in 502 may be image data of the entire brain of a human body, and the user (e.g., a doctor) may be interested in tumors in the brain. In this case, a special display of the tumors (e.g., independent display or highlighted) may be needed.

In some embodiments, the first ROI may also be the entire region corresponding to the medical image data. For example, the user may pay attention to the entire region corresponding to the medical image data and observe an image of the entire region. As disclosed in the present disclosure, an ROI display instruction may refer to an instruction for directing the imaging system 100 to display an ROI in the medical image data on a display device. In some embodiments, the user may input the ROI display instruction through the terminal(s) 130. In some embodiments, the terminal(s) 130 may include an input module through which the user inputs the ROI display instruction. Exemplary input modules may include but not limited to, a mouse, a keyboard, a touch screen, a microphone, etc. The user may input an ROI display instruction (e.g., the first instruction) by various input methods, including but not limited to typing, handwriting, selecting, speaking, etc. In some embodiments, the typing may be in English, in Chinese, or any other languages. The selecting may include selecting from a drop-down list, etc. For example, the user may select an option for displaying tumors in the brain on a list presented on a user interface.

In some embodiments, the first instruction may be used to direct the imaging system 100 to display the first ROI on the display device in a special way (also referred to as special display, which indicates that the first ROI may be displayed with a special display effect, such as highlighted, embossed, hyalinized, etc.). For example, the first ROI may be highlighted when the first ROI is displayed on the display device. In this case, the processing device 140 may highlight the first ROI. Regions other than the first ROI may be displayed in an ordinary way. The first ROI may be highlighted in a color different from the color of other regions. For example, if the medical image data is image data of the brain of a patient, and the first ROI is a cerebral artery of the brain, the first instruction may direct the imaging system 100 to display the cerebral artery in a specific color (e.g., red), which is different from the color of other regions (e.g., light grey).

In some embodiments, the first instruction may be used to direct the imaging system 100 to display the first ROI in an ordinary way (also referred to as ordinary display, which indicates that the first ROI may be displayed without special display effect). In this case, the display device may only display the first ROI instead of displaying the first ROI as well as the regions other than the first ROI. For example, if the medical image data is image data of the heart and the first ROI is a coronary artery in the heart, and the user may pay attention to whether the coronary artery have a stenosis or a plaque, the first instruction may be used to direct the imaging system 100 to display the coronary artery on the display device rather than displaying other regions in the heart. It should be understood that the above embodiments may merely for illustration purposes not intended to limit the scope of the present disclosure, and other display mannners may be used according to specific application scenarios.

In some embodiments, the first ROI may be the entire region corresponding to the medical image data, and the processing device 140 may cause the GPU to render the medical image data directly. In some embodiments, the first ROI may be a part of the region associated with the medical image data, the processing device 140 may extract image data associated with the first ROI (also referred to as first image data) from the medical image data, and cause the GPU to render the first image data. In some embodiments, the processing device 140 may segment the first ROI automatically. Specifically, the processing device 140 may employ various image segmentation algorithms including but not limited to a threshold-based segmentation algorithm, an edge-based segmentation algorithm, a region-based segmentation algorithm, a graph theory-based segmentation algorithm, an energy functional-based segmentation algorithm, a wavelet-based segmentation algorithm, a neural network-based segmentation algorithm, etc. In some embodiments, the first ROI may be segmented by a user manually. For example, a doctor may segment a vertebra from an image of a human body manually. In some embodiments, the first ROI may be segmented using a semi-automatic method. For example, a user may specify a seed point within an outline of the first ROI, and the processing device 140 may segment the first ROI using a region growing algorithm according to the seed point specified by the user.

In 506, first image data associated with the first ROI may be generated according to the first instruction. In some embodiments, the first image data may be generated by the image data generation module 420.

After the first image data is generated, the first image data may be transmitted to the GPU for rendering so as to be displayed on the display device. The first image data may also be referred to as image data to be rendered. In some embodiments, the processing device 140 may designate the image data corresponding to the first ROI in the medical image data as the first image data. Alternatively, the processing device 140 may determine a region encompassing the first ROI, and designate image data corresponding to the region encompassing the first ROI as the first image data. For example, if the medical image data may be CT image data of a human body including ribs and vertebrae, and the first ROI is ribs, the processing device 140 may determine image data of the ribs as the first image data (e.g., segmenting the image data of the ribs from the medical image data using at least one segmentation algorithm described above), or image data of the ribs and vertebrae connecting the ribs as the first image data (e.g., segmenting image data of the vertebrae and the ribs from medical image data). As another example, if the medical image data is MR data of the brain, and the first ROI is a tumor in the brain, the processing device 140 may determine the image data of the tumor as the first image data so as to present an image of the tumor to the user, or image data corresponding to a region within a certain range around the tumor as the first image data, such that the displayed image may include surroundings of the tumor. In some embodiments, the first instruction may direct the imaging system 100 to highlight the first ROI. If the first instruction directs the imaging system 100 to highlight the first ROI, the first image data may further include auxiliary image data that is used to highlight the first ROI.

In 508, the first ROI may be caused to be displayed on the display device as a first image based on the first image data. In some embodiments, the first ROI may be caused to be displayed on the display device as the first image by the transmitting module 440.

The processing device 140 may cause the display device (such as the terminal(s) 130 in FIG. 1, the mobile device 300 in FIG. 3, etc.) to display the first image. The first ROI may be present in the first image. In some embodiments, the processing device 140 may transmit the first image data to the GPU of the display device (e.g., the GPU 330 in mobile device 300 as shown in FIG. 3), which may be rendered by the GPU and displayed on a screen (such as the display 320 in FIG. 3).

In 510, a second instruction for displaying a second ROI on the display device (also referred to as second ROI display instruction) may be obtained. In some embodiments, the second instruction may be obtained by the obtaining module 410.

The second instruction may direct the imaging system 100 to display the second ROI in the medical image data on the display device. In some embodiments, the second ROI may be displayed in a second image on the display device. In a workflow, regions that the user are interested in may be different at different stages. For example, for MR image data of the brain, a region (e.g., the first ROI) that the user is initially interested in may be the entire brain, and a next region (e.g., the second ROI) that the user is further interested in may be a cerebral artery in the brain.

In some embodiments, the second instruction may direct the imaging system 100 to display one second ROI on the display device. In some embodiments, the second instruction may direct the imaging system 100 to display at least two second ROIs on the display device. In some embodiments, the second instruction may be obtained from a user. The user may input the second instruction in various ways, such as typing, handwriting, speaking, etc. In some embodiments, the second instruction may direct the imaging system 100 to display the second ROI in a special way (e.g., highlighted). The second ROI may be segmented from the region corresponding to the medical image data using various segmentation algorithms. In some embodiments, the second ROI may be highlighted in a color different from the color of the first ROI. For example, the second ROI may be highlighted in a green color, and the first ROI may be highlighted in a red color. In some embodiment, the second instruction may direct the imaging system 100 to solely display the second ROI. In some embodiments, the second instruction may direct the imaging system 100 to display the second ROI as well as the first ROI. In some embodiments, the operation 510 may be similar to the operation 504.

In 512, a local region update operation may be performed on the first image data according to the first instruction and the second instruction. In some embodiments, the local region update operation may be performed by the image data updating module 430.

In a workflow, a user may switch, for example, on the display device, from one ROI (e.g., the first ROI) to another (e.g., the second ROI) in the region corresponding to the medical image data. The region corresponding to the medical image data may include the two ROIs. Conventionally, the entire first image data may be updated by the image data updating module 430 in this process. The updated first image data may be rendered by the GPU, and displayed on the display device.

Figure 6A:
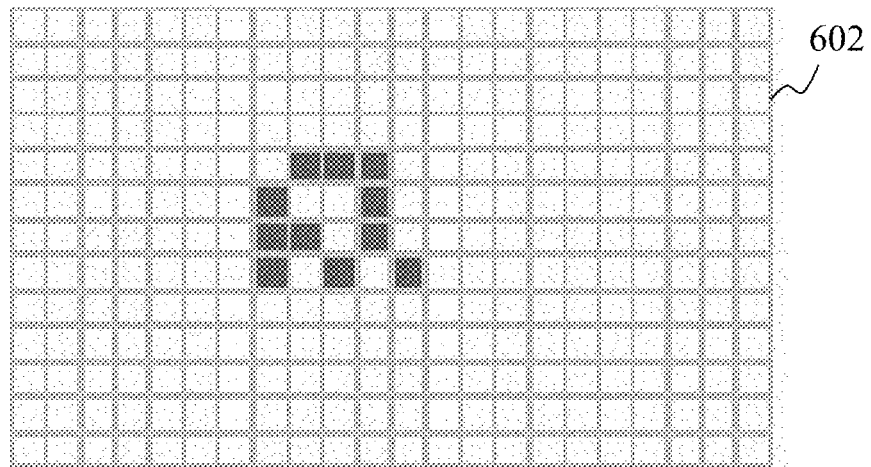
FIGS. 6(a) and 6(b) are schematic diagrams illustrating a conventional image data update process according to some embodiments of the present disclosure.
Figure 6B:
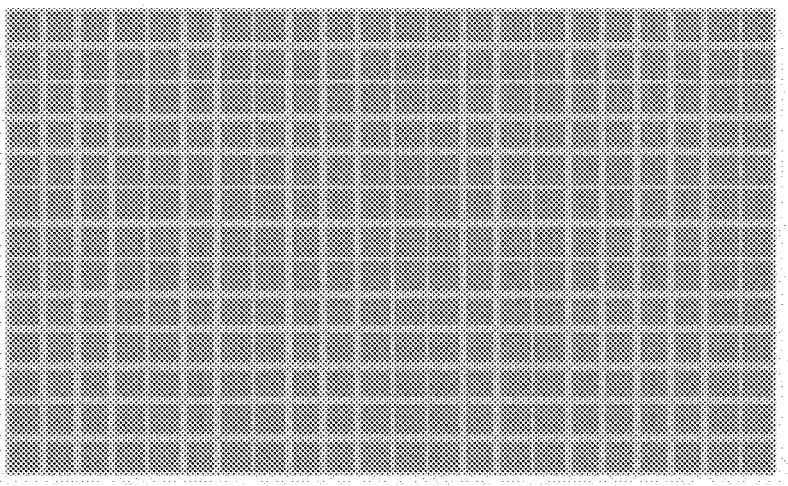

FIGS. 6(*a*) and 6(*b*) are schematic diagrams illustrating a conventional image data update process according to some embodiments of the present disclosure. As shown in FIG. 6(*a*), the pixels in the rectangular box 602 may represent first image data. The first image data may be two-dimensional image data composed of pixels. A part of the first image data may vary in the conventional image data update process. Pixels in the dark grey color represents the image data to be changed, and pixels in the light grey color represents the image data that may not need to be changed. In the conventional image data update process, the entire first image data may be changed, and all the pixels as shown in FIG. 6(*b*) may be in dark grey color. The conventional image data update process may be inefficient and may increase workload of the processing device 140.

However, in many cases, image data of a small part of the region corresponding to the medical image data may need to be changed in the update process to achieve a desired display effect in this process, and image data of other parts of the region may remain unchanged. In some embodiments, the processing device 140 may determine a local region in the region corresponding to the first image data that needs to be updated according to the first instruction and the second instruction. In some embodiments, the processing device 140 may determine elements (e.g., pixels or voxels) to be changed in the first image data according to the first instruction and the second instruction. The elements to be changed may constitute the local region in the first image data that needs to be updated.

In some embodiments, the second ROI may be within the first ROI. If the first instruction directs the imaging system 100 to display the first ROI in the ordinary way, and the second instruction directs the imaging system 100 to display the second ROI in a special way (e.g., highlighted), the first image data may include image data for an ordinary display of the second ROI. In this case, image data regarding the ordinary display of the second ROI in the first image data may need to be substituted by image data for a special display of the second ROI. If both the first instruction and the second instruction direct the imaging system 100 to display the first ROI and the second ROI in the ordinary way or in a special way, image data corresponding to other regions in the first ROI that are outside of the second ROI may be removed from the first image data. For example, if the medical image data is MR data of the brain, and the user is intended to overview the whole brain at first, the first image data may be image data facilitating the ordinary display of the whole brain. Then if the user is intended to observe tumors in the brain in a special way, image data for an ordinary display of the tumors in the first image data may be substituted by image data for a special display of the tumors, and image data of other regions may remain unchanged.

In some embodiments, the first ROI may be within the second ROI, or the first ROI and the second ROI may be isolated ROIs independent from each other. In some embodiments, the two ROIs may be displayed in a same way (e.g., ordinary display or special display), and image data of the second ROI may be added into the first image data. If the user is intended to conceal the first ROI when he/she observes the second ROI, image data of the first ROI may be removed from the first image data. For example, if the medical image data is MR data of the brain, and the user is intended to observe the left ventricle of the brain, the first image data may be image data for an ordinary display of the left ventricle. Then if the user is intended to observe the right ventricle, image data of the right ventricle may be added into the first image data. If the user is intended to conceal the left ventricle when he/she observes the right ventricle, the image data of the left ventricle may be removed from the first image data.

In some embodiments, the first ROI and the second ROI may be partially overlap. In some embodiments, the two ROIs may be displayed in a same way (e.g., ordinary display or special display), and image data of the second ROI may be added into the first image data. If the user is intended to conceal the first ROI when he/she observes the second ROI, one or more overlapping regions of the first ROI and the second ROI may be determined, and image data of remainder regions in the first ROI other than the overlapping regions of the first ROI and the second ROI may be removed from the first image data. For example, if the medical image data is MR data of the brain, and the user is intended to observe the left ventricle, the first image data may be image data for an ordinary display of the left ventricle. If the user is intended to observe a cerebral artery, and the cerebral artery may partially overlap with the left ventricle. In this case, image data of the cerebral artery may be added into the first image data. If the user is intended to conceal the left ventricle when he/she observes the cerebral artery, an overlapping region of the cerebral artery and the left ventricle may be determined, and image data of remainder regions in the first ROI other than the overlapping region of the cerebral artery and the left ventricle may be removed from the first image data.

It may be understood that the local regions in the first image data that need to be updated in the above embodiments are merely for illustration purposes and are not intended to limit the scope of the present disclosure. In some embodiments, the local region in the first image data that need to be updated may be determined according to other relationships between the ways in which the first ROI and the second ROI are displayed. By updating the image data of the local region, an update rate of the image data update process may be increased, the update efficiency of the image data update process may be improved, and the volume of storage may be saved, thereby reducing workloads of the imaging system 100, saving hardware resources, as well as improve the accuracy and efficiency of medical diagnoses.

In some embodiments, the processing device 140 may perform a local region update operation on the first image data using a block region update strategy. The block region update strategy may refer to an update of a region having a block shape in the first image data. The block region update strategy may be suitable for a local region composed of elements needed to be changed having a relatively regular shape.

Figure 7A:
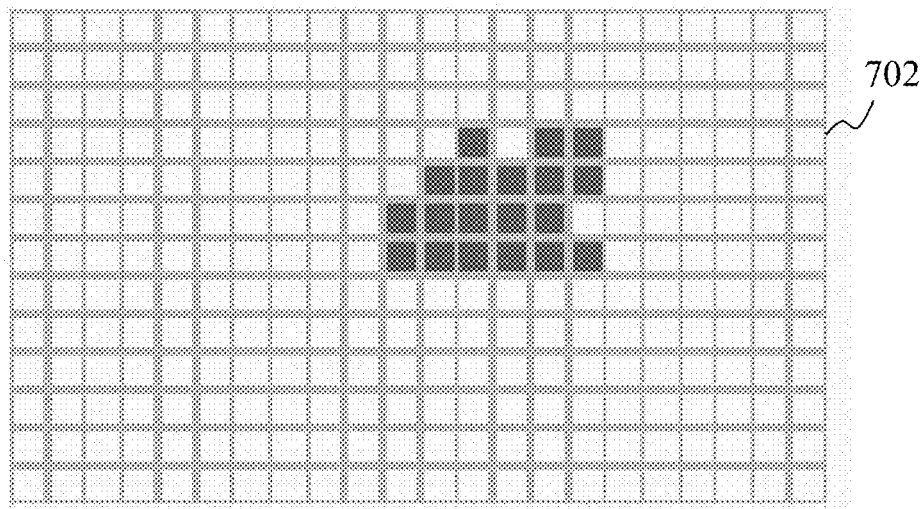
FIGS. 7(a) and 7(b) are schematic diagrams illustrating a local region update operation using the block region update strategy according to some embodiments of the present disclosure.
Figure 7B:
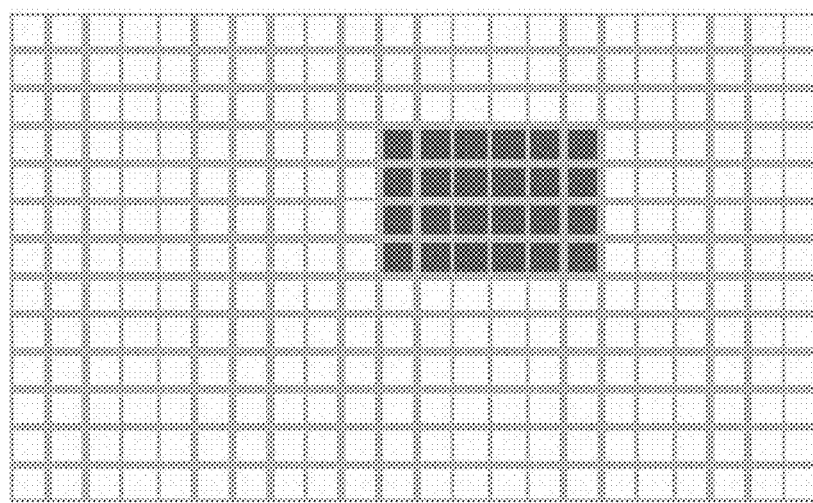

FIGS. 7(a) and 7(b) are schematic diagrams illustrating a local region update operation using the block region update strategy according to some embodiments of the present disclosure. As shown in FIG. 7(a), the pixels in the rectangular box 702 may represent first image data before the local region update operation is performed. The first image data may be medical image data of a person to be rendered by the GPU, which may be segmented and/or labeled in advance. Pixels in the dark grey color represents image data to be changed, and pixels in the light grey color represents the image data that may not need to be changed. Since the pixels in the dark grey color have a relative large degree of aggregation, the block region update strategy may be employed in the update process. During the update process, a block region including the pixels in the dark grey color as illustrated in FIG. 7(a) may be updated. The updated first image data may be shown in FIG. 7(b). As shown in FIG. 7(b), pixels in the dark grey color represents updated pixels. The updated pixels may be in a block shape. In some embodiments, edge elements (e.g., pixels or voxels) that need to be updated in the first image data may be determined, and edges of the block region may be determined according to the edge elements, thereby the block region may be defined. Taking image data of the brain as an example, the user may be intended to observe the entire brain (i.e., the first ROI) at first, then the user may be intended to observe tumors in the brain (i.e., the second ROI) in an image of the entire brain. Image data of the tumors in the first image data may need to be changed in this process. Since the tumors are nearly spherical or ellipsoidal, the shapes of the tumors may be relatively regular, and the elements in the image data may have a larger degree of aggregation, the block region update strategy may be employed in the update process. In some embodiments, an individual region having a block shape in the first image data may be updated. In some embodiments, two or more regions each of which having a block shape in the first image data may be updated. For example, if there are two independent tumors in MR data of the brain, a region having a block shape may be determined for each tumor, and elements in the two regions may be updated.

In some embodiments, the processing device 140 may perform a local region update on the first image data using a discrete region update strategy. The discrete region update strategy may refer to an update of a region having a discrete shape in the first image data. The discrete region update strategy may be suitable for elements needed to be changed having an irregular shape (i.e., discrete pixels or voxels).

Figure 8A:
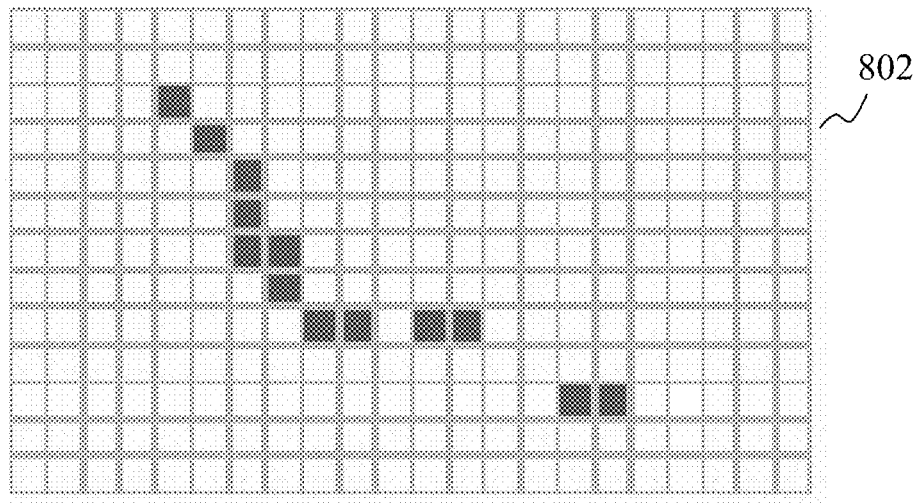
FIGS. 8(a) and 8(b) are schematic diagrams illustrating a local region update operation using the discrete region update strategy according to some embodiments of the present disclosure.
Figure 8B:
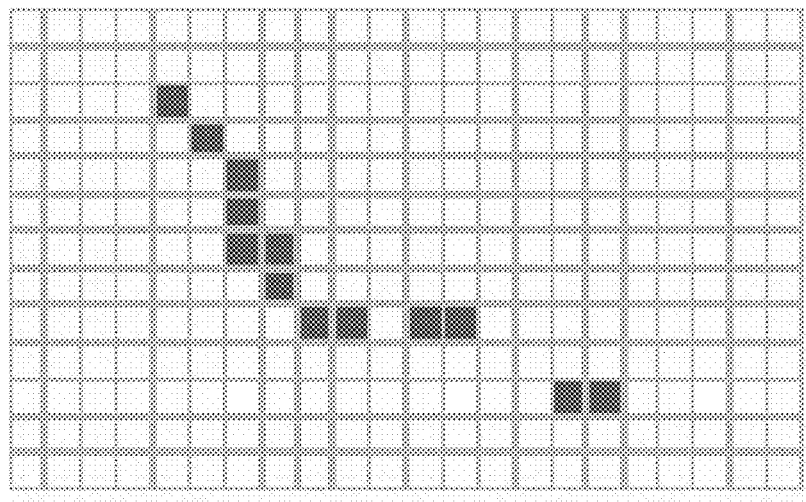

FIGS. 8(a) and 8(b) are schematic diagrams illustrating a local region update operation using the discrete region update strategy according to some embodiments of the present disclosure. As shown in FIG. 8(a), the pixels in the rectangular box 802 may represent first image data before the local region update operation is performed. Pixels in the dark grey color represents image data to be changed, and pixels in the light grey color represents the image data that may not need to be changed. Since the pixels in the dark grey color may be scattered, the discrete region update strategy may be employed in the update process. During the update process, a discrete region including the pixels in the dark grey color as illustrated in FIG. 8(a) may be updated. The updated first image data may be shown in FIG. 8(b). As shown in FIG. 8(b), pixels in the dark grey color represents updated pixels, which are discrete pixels having a same shape as the pixels to be updated in FIG. 8(a). Taking image data of the brain as an example, the user may be intended to observe the entire brain (i.e., the first ROI), then the user may be intended to observe an cerebral artery (i.e., the second ROI) in an image of the entire brain. Image data of the cerebral artery in the first image data may need to be changed in this process. Since the cerebral artery has a shape of a slender tube, the shape of the cerebral artery may be irregular, and the elements in the image data may be relatively scattered, the discrete region update strategy may be employed in the update process. In some embodiments, for cases where the second instruction directs the imaging system 100 to display at least two second ROIs as a second image on the display device, a same update strategy or different update strategies may be employed according to different second ROIs. For example, if a second instruction directs the imaging system 100 to display two second ROIs including a tumor and a cerebral artery in the brain. A block region update strategy may be employed for the tumor, and a discrete region update strategy may be employed for the cerebral artery.

In some embodiments, the strategies for the local region update (e.g., the block region update strategy or the discrete region update strategy) may be preset, for example, by the user, according to default settings of the imaging system 100, etc. The strategies for the local region update may determine whether the local region is a region having a block shape or a region having a discrete shape. In some embodiments, the user may determine a strategy for the local region update based on apriori knowledge. For example, since arteries are generally irregular in shape, and elements constituting the arteries are relatively discrete, the discrete region update strategy may be employed. As another example, since a tumor is generally regular in shape and elements constituting the tumor are relatively concentrated, the block region update strategy may be employed. In some embodiments, the processing device 140 may determine a strategy for the local region update automatically. Specifically, the processing device 140 may determine elements to be changed in the first image data according to the first instruction and the second instruction, and determine the strategy for the local region update according to the positions of the elements automatically. For example, a dispersion degree between the elements may be calculated based on coordinates of the elements. If the dispersion degree exceeds a preset threshold, the strategy for the local region update may be determined as the discrete region update strategy. If the dispersion degree does not exceed the preset threshold, the strategy for the local region update may be determined as the block region update strategy. In some embodiments, the user may also specify the strategy for the local region update when he/she inputs the ROI display instruction (e.g., the first ROI display instruction or the second ROI display instruction) into the imaging system 100. By determining the strategy for the local region update according to the shape and/or concentration of elements of the local region corresponding to the image data to be changed, the efficiency of the image data update may be improved and a better update effect may be achieved.

In some embodiments, the medical image data may include volume data and mask data. The mask data may be used to process volume data to achieve a specific display effect. The first mage data (i.e., image data to be rendered) may include the volume data and appropriate mask data. In order to display the second ROI after the first ROI is displayed, the mask data may need to be updated, and the volume data may remain unchanged. In some embodiments, the local regions of the mask data may be updated to facilitate a desired display effect. In some embodiments, the local region update of the mask data may be similar to or the same as the local region update operation described above.

In some embodiments, the way that the image data is updated and/or displayed may be customized according to the user's habits. Merely by ways of example, each user may have a user account, and the user may log in his or her user account when he/she operates the imaging system 100 or a part of the imaging system 100 (e.g., the imaging scanner 110). The processing device 140 may record historical operations (e.g., an ROI display instruction) of the user, and the way in which the image data is updated and/or displayed may be determined based on the historical operations of the user. For example, a user's historical operations on image data of the brain may reveal that the user may be accustomed to a simultaneous display of the entire brain when he/she observes the cerebral artery in the brain, and the cerebral artery may be highlighted. According to the user's historical operations, next time when the user observes an image of the brain and before he/she inputs an ROI display instruction for displaying the cerebral artery, the cerebral artery may be displayed in a special way and other regions of the brain may be displayed in an ordinary way. As another example, a user's historical operations on image data of the torso may reveal that the user may be accustomed to a simultaneous display of the vertebrae and ribs he/she observes the vertebrae and ribs at first, then the vertebrae or the ribs may be displayed independently. According to the user's historical operations, next time when the user observes an image of the torso and before he/she inputs an ROI display instruction for displaying the vertebra or the ribs, the first image data may be generated to facilitate the simultaneous display of the vertebrae and ribs, and the updated first image data may be generated to facilitate the independent display the ribs or vertebrae. In this way, personalized needs of the user may be satisfied, and a better user experience may be provided.

In 514, the second ROI may be caused to to be displayed on the display device as a second image based on the updated first image data. The processing device 140 may send the updated first image data generated through the local region update to the GPU of the display device, and the second ROI may be displayed on the display device after the GPU renders the updated first image data. In some embodiments, the operation 514 may be similar to or the operation 508.

It should be noted that the description of the process 500 may be provided for illustration purposes and may not limit the scope of the present disclosure. Various modifications and changes to the process 500 may be made by those skilled in the art under the teaching of the present disclosure. However, these modifications and changes may still be within the scope of the present disclosure. For example, after the operation 514 is performed, a third ROI display instruction (also referred to as third instruction) input by the user may be received, a local region update operation may be performed on the updated first image data according to the second instruction and the third instruction, and a third ROI may be displayed.

Figure 9:
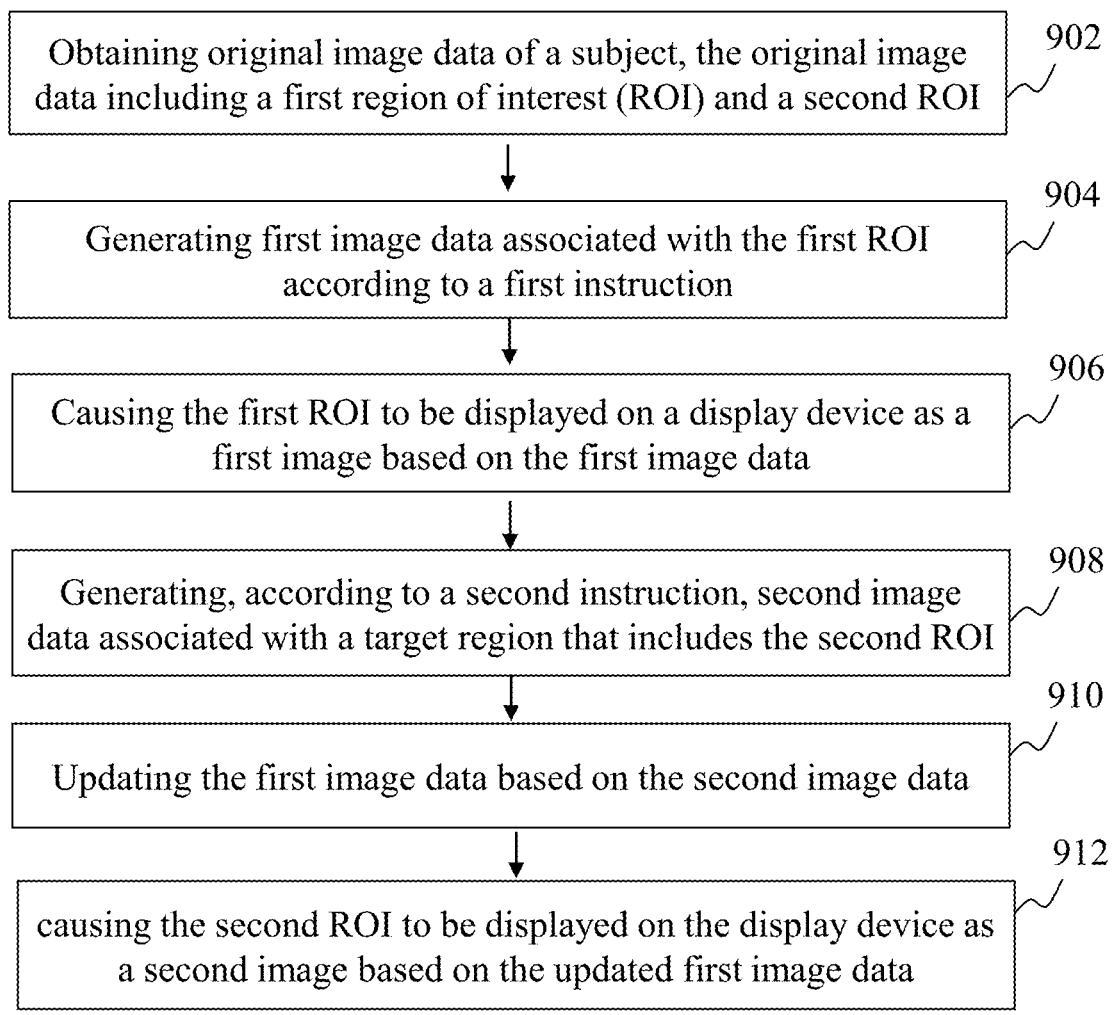
FIG. 9 is flowchart illustrating an exemplary process for displaying image data of multiple ROIs according to some embodiments of the present disclosure.

FIG. 9 is flowchart illustrating an exemplary process for displaying image data of multiple ROIs according to some embodiments of the present disclosure. In some embodiments, at least a portion of the process 900 may be executed by the processing device 140 (e.g., implemented in the computing apparatus 200 shown in FIG. 2, the processing device illustrated in FIG. 4). In some embodiments, the process 900 may be executed by a cloud server so as to reduce the working load of the processing device 140. In some embodiments, at least a portion of the process 900 may be executed by a terminal device (e.g., the mobile device 300 shown in FIG. 3) embodying software and/or hardware.

In 902, original image data of a subject may be obtained. The original image data including a first region of interest (ROI) and a second ROI. In some embodiments, the original image data may be obtained by the obtaining module 410. In some embodiments, the operation 902 may be similar to or the same as the operation 502 of the process 500 as illustrated in FIG. 5.

The original image data may be two-dimensional (2D) image data or three-dimensional (3D) image data. The original image data in the present disclosure may have various types including but not limited to, computed tomography (CT) image data, emission computed tomography (ECT) image data, magnetic resonance (MR) image data, ultrasound image data, positron emission tomography (PET) image data, or the like.

The original image data may include at least two ROIs including, for example, a first ROI, a second ROI, a third ROI, etc. Taking original image data of the brain as an example, the original image data of the brain may include ROIs of the entire brain, the thalamus, the putamen, the insula, the thalamus, the globus pallidus, the frontal lobe, the parietal lobe, the pituitary, the cerebrovascular, etc. Positions between each two of the ROIs may be in various relationships, such as partially overlapping, independent of each other, containment, or the like.

In 904, first image data associated with the first ROI may be generated according to a first instruction. In some embodiments, the first image data may be generated by the image data generating module 420. In some embodiments, the operation 904 may be similar to or the same as a combination of the operation 502 and the operation 504 of the process 500 as illustrated in FIG. 5.

The first image data may be image data associated with the first ROI. The first ROI may be segmented from a region corresponding to the original image data. In some embodiments, the processing device 140 may segment the first ROI automatically. Specifically, the processing device 140 may employ various image segmentation algorithms including but not limited to a threshold-based segmentation algorithm, an edge-based segmentation algorithm, a region-based segmentation algorithm, a graph theory-based segmentation algorithm, an energy functional-based segmentation algorithm, a wavelet-based segmentation algorithm, a neural network-based segmentation algorithm, etc. In some embodiments, the first ROI may be segmented by a user manually. For example, a doctor may segment a vertebra from an image of a human body manually. In some embodiments, the first ROI may be segmented using a semi-automatic method. For example, a user may specify a seed point within an outline of the first ROI, and the processing device 140 may segment the first ROI using a region growing algorithm according to the seed point specified by the user.

In some embodiments, the processing device 140 may designate the image data corresponding to the first ROI in the medical image data as the first image data. Alternatively, the processing device 140 may determine a region encompassing the first ROI, and designate image data corresponding to the region encompassing the first ROI as the first image data.

The first instruction may direct the imaging system 100 to display the first ROI in the medical image data on the display device. In some embodiments, the first instruction may be used to direct the imaging system 100 to display the first ROI on the display device in a special way (e.g., highlighted, embossed, hyalinized, etc.). In some embodiments, the first instruction may be used to direct the imaging system 100 to display the first ROI in an ordinary way.

In 906, the first ROI may be caused to be displayed on a display device as a first image based on the first image data. In some embodiments, the first ROI may be transmitted to the display device by the transmitting module 440. In some embodiments, the operation 906 may be similar to or the same as the operation 508 of the process 500 as illustrated in FIG. 5. In some embodiments, the first ROI may be displayed on the display device in a special way (e.g., highlighted, embossed, hyalinized, etc.). For example, the first ROI may be highlighted in a color different other regions in the original image data. In some embodiments, the first ROI may be displayed on the display device in an ordinary way.

The processing device 140 may cause the display device (such as the terminal(s) 130 in FIG. 1, the mobile device 300 in FIG. 3, etc.) to display the first image. The first ROI may be present in the first image. In some embodiments, the processing device 140 may transmit the first image data to the GPU of the display device (e.g., the GPU 330 in mobile device 300 as shown in FIG. 3), which may be rendered by the GPU and displayed on a screen (such as the display 320 in FIG. 3).

In 908, second image data corresponding to a target region that includes the second ROI may be generated according to a second instruction. In some embodiments, the second image data may be generated by the image data generation module 420.

In some embodiments, the second ROI may be segmented from the first image. In some embodiments, the processing device 140 may segment the second ROI automatically. Specifically, the processing device 140 may employ various image segmentation algorithms including but not limited to a threshold-based segmentation algorithm, an edge-based segmentation algorithm, a region-based segmentation algorithm, a graph theory-based segmentation algorithm, an energy functional-based segmentation algorithm, a wavelet-based segmentation algorithm, a neural network-based segmentation algorithm, etc. In some embodiments, the second ROI may be segmented in the first image by a user manually. For example, a doctor may segment a vertebra from the first image manually. In some embodiments, the second ROI may be segmented using a semi-automatic method. For example, a user may specify, on the first image, a seed point within an outline of the second ROI, and the processing device 140 may segment the second ROI using a region growing algorithm according to the seed point specified by the user.

The target region may include the second ROI. In some embodiments, the shape of the target region may be determined based at on a shape of the second ROI. In some embodiments, elements (pixels or voxels) constituting the second ROI may have a larger degree of aggregation. For example, a dispersion degree between the elements calculated based on coordinates of the elements may be larger than a preset threshold. The second ROI may be determined to have a block shape. In this case, the target region may have a block shape encompassing the second ROI. For example, a minimum rectangular box constituted by elements that encompasses the second ROI may be determined as the target region.

In some embodiments, elements (pixels or voxels) constituting the second ROI may have a smaller degree of aggregation, such as scattered pixels. For example, the dispersion degree between the elements calculated based on coordinates of the elements may be smaller than or equal to the preset threshold. The second ROI may be determined to have a discrete shape. In this case, the target region may have a discrete shape that is the same as the second ROI. The image data corresponding to the target region may be determined as the second image data.

In 910, the first image data may be updated based on the second image data. In some embodiments, the first image data may be updated by the image data updating module 430. In some embodiments, the operation 910 may be similar to or the same as the operation 512 of the process 500 as illustrated in FIG. 5.

In some embodiments, the target region may be within the first ROI. The first image data may be updated by substituting image data corresponding to the target region in the first image data by the second image data.

In some embodiments, the first ROI and the target region may be isolated regions independent from each other. The first image data may be updated by adding the second image data into the first image data.

In some embodiments, the first ROI and the target region may be partially overlap. One or more overlapping regions of the first ROI and the target region may be determined. The first image data may be updated by adding the second image data into the first image data and removing a portion of the first image data that corresponds to the overlapping region from the first image data.

In 912, the second ROI may be caused to be displayed on the display device as a second image based on the updated first image data. In some embodiments, the second ROI may be transmitted to the display device by the transmitting module 440. In some embodiments, the operation 912 may be similar to or the same as the operation 514 of the process 500 as illustrated in FIG. 5.

The processing device 140 may cause the display device (such as the terminal(s) 130 in FIG. 1, the mobile device 300 in FIG. 3, etc.) to display the second image. The second ROI may be present in the second image. In some embodiments, the processing device 140 may transmit the updated first image data to the GPU of the display device (e.g., the GPU 330 in mobile device 300 as shown in FIG. 3), which may be rendered by the GPU and displayed on a screen (such as the display 320 in FIG. 3). In some embodiments, the second ROI may be displayed on the display device in a special way (e.g., highlighted, embossed, hyalinized, etc.). For example, the second ROI may be highlighted in a color different from the color of other regions including the first ROI. In some embodiments, the second ROI may be displayed on the display device in an ordinary way. For example, the second ROI may be displayed in the second image in an ordinary way, and other regions may be concealed in the second image.

It should be noted that the description of the process 500 may be provided for illustration purposes and may not limit the scope of the present disclosure. Various modifications and changes to the process 500 may be made by those skilled in the art under the teaching of the present disclosure. However, these modifications and changes may still be within the scope of the present disclosure. For example, the process 900 may further include operations such as obtaining the first instruction and/or the second instruction.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or feature described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or features may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for medical image visualization, comprising:
   at least one storage medium including a set of instructions; and
   at least one processor configured to communicate with the at least one storage medium, wherein when executing the set of instructions, the system is directed to perform operations including:
   obtaining original image data of a subject, the original image data including a first region of interest (ROI) and a second ROI;
   generating first image data associated with the first ROI according to a first instruction;
   causing the first ROI to be displayed on a display device as a first image based on the first image data;
   generating, according to a second instruction, second image data corresponding to a target region that includes the second ROI;
   determining, based on coordinates of a plurality of elements constituting the second ROI, a dispersion degree between the elements;
   determining, based on the dispersion degree, a strategy between a block region update strategy and a discrete region update strategy;
   updating, based on the second image data and the strategy, the first image data by performing a local region update operation; and
   causing the second ROI to be displayed on the display device as a second image based on the updated first image data.

2. The system of claim 1, the causing the first ROI to be displayed on the display device as a first image based on the first image data including:
   causing a rendering device associated with the display device to render the first image data; and
   causing the display device to display the first ROI in the first image based on the rendered first image data.

3. The system of claim 1, wherein the second instruction is generated based on the first image.

4. The system of claim 1, the causing the second ROI to be displayed on the display device as a second image based on the updated first image data including:
   causing a rendering device associated with the display device to render the updated first image data; and
   causing the display device to display the second ROI in the second image based on the rendered updated first image data.

5. The system of claim 1, the operations further including:
   segmenting the first ROI from the original image data according to the first instruction; and
   segmenting the second ROI from the original image data according to the second instruction.

6. The system of claim 5, wherein the target region has a discrete shape that is the same as the second ROI or a block shape encompassing the second ROI.

7. The system of claim 6, wherein the shape of the target region is determined based at least in part on a shape of the second ROI.

8. The system of claim 1, wherein the original image data includes volume data, and the first image data and the second image data includes mask data.

9. The system of claim 1, the causing the first ROI to be displayed on the displaying device as a first image based on the first image data including:
   causing the first ROI to be displayed on the displaying device in a first color different from other regions in the first image.

10. The system of claim 9, the causing the second ROI to be displayed on the displaying device as a second image based on the updated first image data including:
    causing the second ROI to be displayed on the displaying device in a second color different from the first color in the first image.

11. The system of claim 1, the performing a local region update operation including:
    substituting image data corresponding to the target region in the first image data by the second image data.

12. The system of claim 1, the performing a local region update operation including:
    adding the second image data into the first image data.

13. The system of claim 1, the performing a local region update operation including:
    adding the second image data into the first image data and removing a portion of the first image data that corresponds to an overlapping region from the first image data.

14. A method for medical image visualization, implemented on a computing device having a processor and a computer-readable storage device, the method comprising:

obtaining original image data of a subject, the original image data including a first region of interest (ROI) and a second ROI;

generating first image data associated with the first ROI according to a first instruction;

causing the first ROI to be displayed on a display device as a first image based on the first image data;

generating, according to a second instruction, second image data corresponding to a target region that includes the second ROI;

determining, based on coordinates of a plurality of elements constituting the second ROI, a dispersion degree between the elements;

determining, based on the dispersion degree, a strategy between a block region update strategy and a discrete region update strategy;

updating, based on the second image data and the strategy, the first image data by performing a local region update operation; and causing the second ROI to be displayed on the display device as a second image based on the updated first image data.

15. The method of claim 14, wherein the second instruction is generated based on the first image.

16. The method of claim 14, the causing the second ROI to be displayed on the display device as a second image based on the updated first image data including:

causing a rendering device associated with the display device to render the updated first image data; and causing the display device to display the second ROI in the second image based on the rendered updated first image data.

17. The method of claim 14, further including:

segmenting the first ROI from the original image data according to the first instruction; and segmenting the second ROI from the original image data according to the second instruction.

18. The method of claim 17, wherein the target region has a discrete shape that is the same as the second ROI or a block shape encompassing the second ROI.

19. The method of claim 18, wherein the shape of the target region is determined based at least in part on a shape of the second ROI.

20. A non-transitory computer readable medium, comprising at least one set of instructions, wherein when executed by at least one processor of a computing device, the at least one set of instructions causes the computing device to perform a method for medical image visualization, the method comprising:

obtaining original image data of a subject, the original image data including a first region of interest (ROI) and a second ROI;

generating first image data associated with the first ROI according to a first instruction;

causing the first ROI to be displayed on a display device as a first image based on the first image data;

generating, according to a second instruction, second image data corresponding to a target region that includes the second ROI;

determining, based on coordinates of a plurality of elements constituting the second ROI, a dispersion degree between the elements;

determining, based on the dispersion degree, a strategy between a block region update strategy and a discrete region update strategy;

updating, based on the second image data and the strategy, the first image data by performing a local region update operation; and causing the second ROI to be displayed on the display device as a second image based on the updated first image data.

* * * * *